Figure 1:
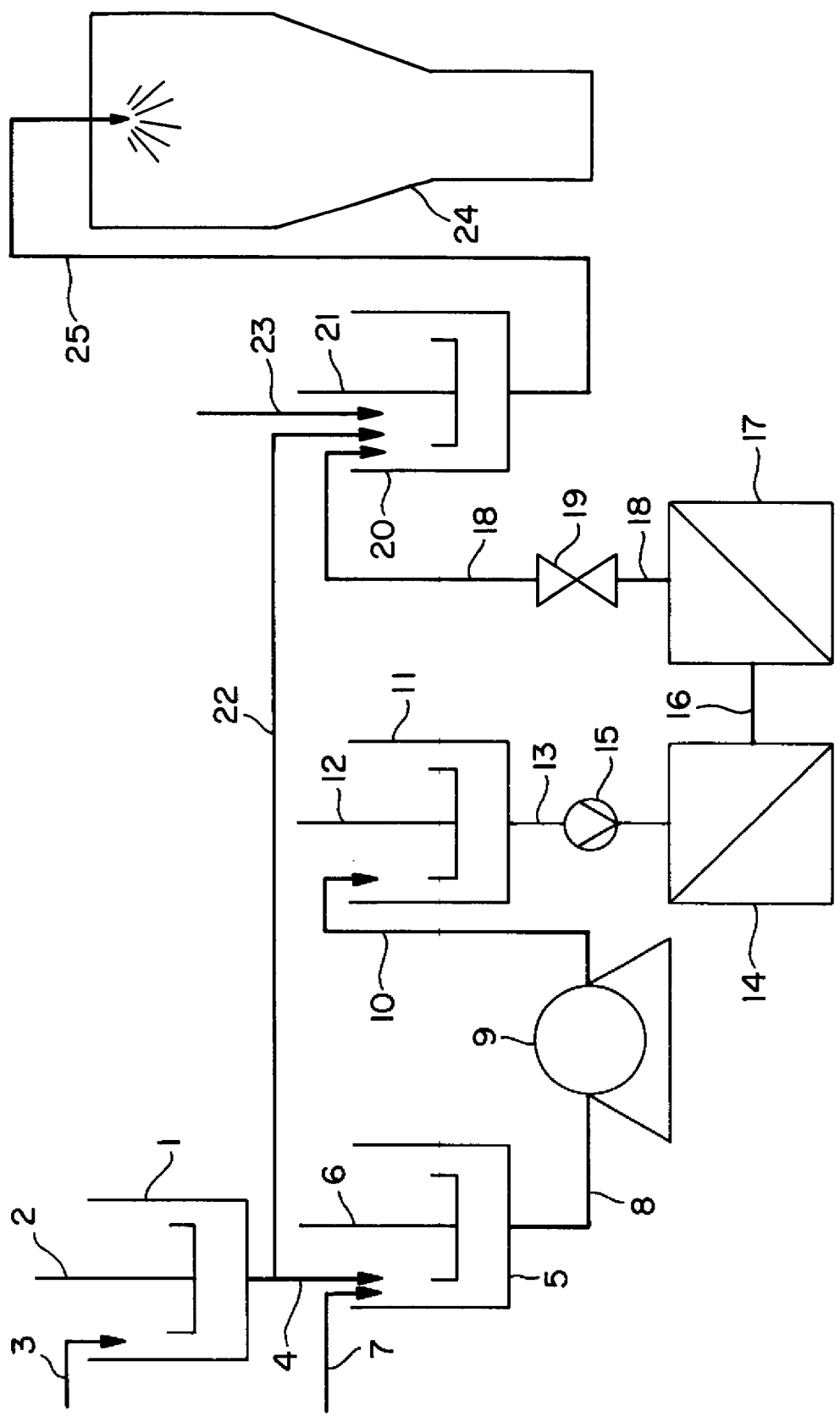

United States Patent
Vilstrup et al.

[11] Patent Number: 5,811,609
[45] Date of Patent: Sep. 22, 1998

[54] PROCESS FOR THE PREPARATION OF A WATER DISPERSIBLE CAROTENOID PREPARATION IN POWDER FORM

[75] Inventors: Per Vilstrup, Farum; Nina Musaeus Jensen, Hellerup; Sven Krag-Andersen, Gentofte, all of Denmark

[73] Assignee: Danochemo A/S, Ballerup, Denmark

[21] Appl. No.: 501,057

[22] PCT Filed: Feb. 21, 1994

[86] PCT No.: PCT/DK94/00072

§ 371 Date: Aug. 30, 1995

§ 102(e) Date: Aug. 30, 1995

[87] PCT Pub. No.: WO94/19411

PCT Pub. Date: Sep. 1, 1994

[30] Foreign Application Priority Data

Feb. 19, 1993 [DK] Denmark .................................. 0193/93

[51] Int. Cl.⁶ .......................... C07C 403/00; C07C 403/24
[52] U.S. Cl. ............................................................ 585/351
[58] Field of Search ............................................... 585/351

[56] References Cited

U.S. PATENT DOCUMENTS 5,453,447 9/1995 End et al. ................................ 585/351

FOREIGN PATENT DOCUMENTS

| 154395 | 11/1982 | Denmark ................... A23L 1/275 |
| 0410236 | 1/1991 | European Pat. Off. ....... A61K 3/015 |
| 523024 | 7/1972 | Switzerland ................. A23K 1/16 |

*Primary Examiner*—Glenn A. Caldarola
*Assistant Examiner*—Alexander G. Ghyka
*Attorney, Agent, or Firm*—Watson Cole Stevens Davis, P.L.L.C.

[57] ABSTRACT

A powdered water-dispersible carotenoid preparation in the form of discrete carotenoid microparticles is prepared by milling a carotenoid in an aqueous medium in the presence of a hydrocolloid so as to form a suspension, heating the suspension thus formed to a sufficiently high temperature to cause a total or partial melting of the carotenoid and cooling, finely dividing and drying the suspension to form a powder.

9 Claims, 2 Drawing Sheets

PROCESS FOR THE PREPARATION OF A WATER DISPERSIBLE CAROTENOID PREPARATION IN POWDER FORM

The present invention relates to a process for the preparation of a powdered, water-dispersible carotenoid preparation in the form of discrete carotenoid microparticles.

The carotenoids form a group of organic chemical compounds which have colours varying from yellow to red and which are widely used as dyes. Examples of carotenoids which are suitable as dyes are β-carotene, lycopene, bixin, zeaxanthine, cryptoxanthine, lutein, canthaxantine, astaxanthine, β-apo-8'-carotenal, β-apo-12'-carotenal and derivatives thereof.

Carotenoids are also suitable for use in pharmaceutical preparations and in food products and feeds.

The carotenoids which are insoluble in water are sensitive to oxidation, and it is well-known to encapsulate carotenoid particles in various matrix materials which have been selected in such a manner that the matrix material is dissolved and releases the carotenoid particles when the encapsulated particles are stirred into a suitable medium at a suitable temperature, for example water or artificial intestinal juice.

It is well-known that the colour intensity of a carotenoid dye or pigment which is dispersed in an aqueous medium increases with decreasing particle size and that also the bioavailability of biologically active carotinoides increases with decreasing particle size.

Numerous attempts have been made to improve the colour intensity and the bioavailability of carotenoid preparations. Thus, DK patent specification No. 154395 discloses a process for the preparation of finely divided powdered carotenoid preparations in which the carotenoid has a particle size of below 5 $\mu$m by dissolving the carotenoid in a volatile water-immiscible organic solvent and by mixing the solution thus obtained with an aqueous solution of a colloid so as to cause colloid-disperse particles to be precipitated and by subsequently separating the particles from the solvent.

CH-A-523 024 discloses another process which is based on the use of a solvent for the carotenoid. In said process the carotenoid is dissolved in a vitamin A, vitamin E or a derivative thereof and the solution thus obtained is emulsified in an aqueous solution, whereafter the emulsion is converted into a dry powder by spray drying.

This prior art process suffers from the drawback that an organic solvent has to be used in the preparation of the carotenoid powder. This is undesirable when the carotenoid is to be used in medicines or food products.

In another well-known process, cf. EP patent application No. 0410236-A2 for the preparation of colloid-disperse carotenoid preparations a suspension of a carotenoid in a high-boiling oil is contacted with superheated steam for a period of no more than 30 seconds whereafter the mixture thus obtained is emulgated in an aqueous mixture of a colloid and the emulsion thus obtained is sprayed and dried.

A significant drawback of this prior art process is that the carotenoid preparation formed inevitably contains the high-boiling oil used. In this manner the maximum obtainable concentration of the carotenoid in the encapsulated product is limited.

The process of the invention comprises the steps of milling a carotenoid in an aqueous medium in the presence of a hydrocolloid to form a suspension and finely dividing and drying the suspension thus obtained so as to form a powder, and the process is characterized in heating the suspension formed by the milling to a temperature sufficiently high to cause a total or partial melting of the carotenoid and subsequently cooling the suspension before it is converted into a powder.

The invention is based on the discovery that the above-mentioned heat treatment results in a product in which the carotenoid is present in essentially amorphous state which has been demonstrated by X-ray diffraction and that the amorphous carotenoid thus formed has a higher bioavailability than crystalline carotenoid.

The heating of the suspension of milled cartenoide in the aqueous hydrocolloid solution is preferably effected at a temperature slightly above the melting point of the carotenoid and this temperature is preferably maintained only for such a period that all carotenoid particles have been molten. Thus, heating over extended periods of time to the high temperature can result in a decomposition of both the carotenoid and the hydrocolloid.

Ordinarily it is preferred that the high temperature is maintained for a period of time of from 0.05 to 200 seconds, preferably from 0.2 to 100 seconds.

When preparing a β-carotene preparation by the process of the invention the suspension is preferably heated to a temperature of from 150° to 200° C. for a period of from 5 to 150 seconds.

The cooling of the hot suspension is preferably effected quickly partly to freeze the amorphous state and partly to avoid decomposition of the carotenoid and/or the hydrocolloid.

The preparation of the carotenoid containing mixture which is to be milled is preferably effected by initially mixing water and a hydrocolloid and optionally an antioxidant. Carotenoid, e.g. in the form of carotenoid crystals, is then added to the mixture thus formed or a portion thereof before the mixture thus obtained is milled. The milling is preferably effected in a pearl mill or a similar mill provided with cooling means so that the temperature can be maintained at a sufficiently low value to prevent decomposition of the carotenoid or the hydrocolloid. During the milling the materials are preferably kept under a controlled atmosphere.

When the milling has been effected the suspension is preferably passed to a storage container and further on to a high-pressure pump which is connected to a heat source, e.g. a heat exchanger. Alternatively, heat may be supplied by steam injection, electrical heating, microwaves or induction. By using a back-pressure valve and the high-pressure pump the pressure is increased to a sufficiently high value to prevent that the liquid boils during the heating effected in the heat exchanger. Following the heating of the suspension to the above-mentioned temperature the hydrocolloid is added and optionally also an additive, e.g. sugar, before it is quickly cooled, e.g. by flash-evaporation, to a temperature between room temperature and 100° C. Following the cooling the suspension is passed to a pressure relief valve in which the pressure is reduced to atmospheric pressure. Subsequently the suspension can be passed to a storage container before it is converted into a powder, e.g. in a spray drying apparatus. Before the milled and heat-treated suspension is converted into a powder in for example a spray drying apparatus a matrix auxiliary agent, such as sugar, is preferably added.

As mentioned above, carotenoid can be added to only part of the mixture of water and colloid and optionally anti-oxidant to be milled and heat-treated.

The remaining part of the mixture is preferably combined with the carotenoid-containing part following the heat treatment of same, e.g. in the above-mentioned storage container.

This embodiment presents the advantage that only part of the hydrocolloid is subjected to the severe heat-treatment. In this manner the decomposition of the protecting hydrocolloid is limited.

Examples of hydrocolloids which are suitable for use in the process of the invention are the hydrocolloids which are mentioned on pages 4–5 of international patent publication No. WO91/06292. Further examples of suitable hydrocolloids are sugarbeet pectin, amidated pectin and fish gelatin.

The amount of hydrocolloid is normally not below 1% by weight of the carotenoid and preferably not less than 10–15% by weight. The amount used should preferably be sufficient to obtain a complete moistening and consequently protection of the carotenoid.

The process of the invention is suitable for the preparation of a series of carotenoid preparations, such as preparations consisting of or containing the carotenoids mentioned above.

Further examples of such carotenoids are annatto, norbixin, capsanthine, capsorubine, flavoxanthine, rubixanthine, violaxanthine, rhodoxanthine, citranaxanthine and derivatives thereof.

The steps of finely dividing and drying the suspension containing the milled and heat-treated carotenoid can be effected in a manner which is well-known per se, e.g. by spray-cooling, spray-drying, modified spray-drying or plate drying and crushing. Some of these methods are mentioned on pages 5–7 international patent publication No. WO/91/06292.

Figure 2:
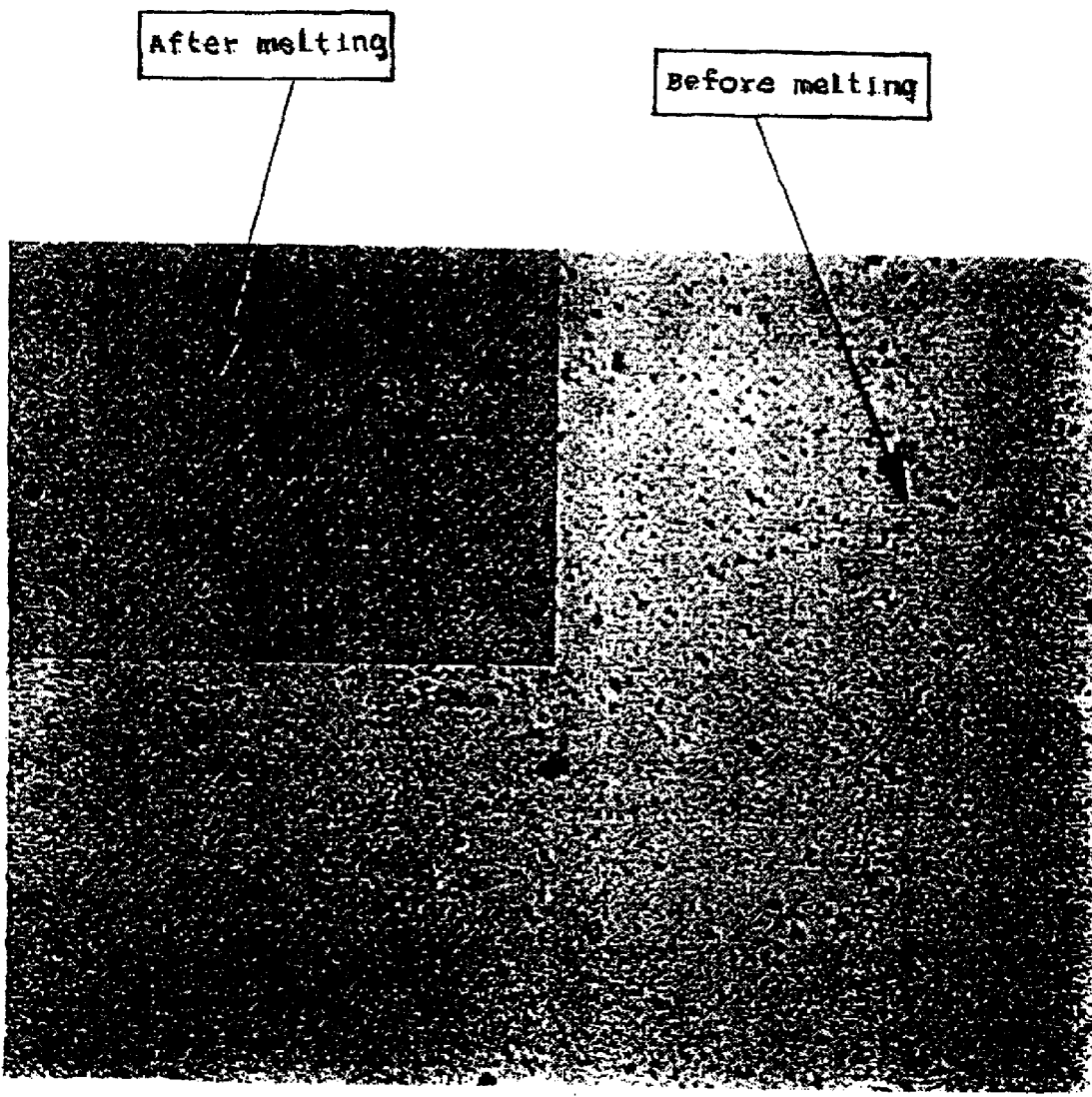

The invention will now be described in further detail with reference to the drawings in which FIG. 1 shows a flow sheet of a preferred embodiment of the process according to the invention, and FIG. 2 shows a microphotograph of canthaxantine particles before and after the heat treatment mentioned in Example 8.

In FIG. 1, 1 designates a mixing tank provided with a stirrer 2 and a conduit 3 for the supply of water, hydrocolloid and additives, such as anti-oxidant, if any. A conduit 4 connects the mixing tank 1 with a tank 5 comprising a stirrer 6 and a conduit 7 for the supply of carotenoid, e.g. β-carotene crystals. A conduit 8 connects the tank 5 with the inlet of a mill 9 having an outlet which is connected with a tank 11 through a conduit 10. The tank 11 is provided with a stirrer 12. A conduit 13 connects the tank 11 with a high-temperature heat exchanger 14 through a high-pressure pump 15. A conduit 16 connects the high-temperature heat exchanger 14 with a flow-through cooler 17. A conduit 18 in which there is provided a relief valve 19 connects the outlet of the cooler 17 with a further tank 20 provided with a stirrer 21. A conduit 22 connects the tank 20 with the conduit 4 and the tank 20 comprises a conduit 23 for the supply of matrix auxiliary agent, such as sugar. The tank 20 is also connected with a spray-drying apparatus 24 through a conduit 25.

After admixing water, hydrocolloid and additives, if any, in the mixing tank, the mixture formed is divided into two streams, one of these streams, e.g. constituting about 25% of the total mixture, being passed to the tank 5 whereas the remaining part is passed to the tank 20 through the conduit 22. Following addition of carotenoid in the tank 5 the mixture thus formed is introduced into the mill 9 in which the carotenoid particles are milled to obtain an average particle size which preferably is below 10 μm. The milled mixture passes then to the tank 11 and from this tank through the high-pressure pump 15 to the high-temperature heat exchanger 14 in which it is heated to a temperature of e.g. 180°–190° C. for a period of 15–90 seconds and is subsequently quickly cooled in the flow-through cooler 17.

The cooled suspension is then passed to the tank 20 and the mixture supplied through the conduit 22 and matrix auxiliary agent supplied through the conduit 23 are added to the cooled suspension before the mixture thus obtained is passed through the conduit 25 to the spray-drying apparatus 24 in which it is converted into a fine powder.

The invention will now be described in further detail with reference to the following

EXAMPLES

Example 1

A suspension of

| | |
|---|---|
| Water | 707.1 g |
| Gelatine 240 bloom, acid-hydrolyzed | 104.4 g |
| Sodium ascorbate | 14.0 g |
| β-Carotene crystals | 139.6 g | milled in a pearl mill to obtain β-carotene particles having an average particle size of below 10 μm is subjected to high-temperature heating by means of a tubular heat exchanger under pressure and subsequent cooling to 65° C. and pressure relief to atmospheric pressure under the conditions set forth in the following Table 1. The milled and heat-treated suspension was then mixed with a matrix solution having the following composition:

| | |
|---|---|
| Water | 457.0 g |
| Gelatine 240 bloom | 210.8 g |
| Sugar | 248.7 g |
| Sodium ascorbate | 4.6 g |
| Ascorbyl palmitate | 15.0 g |
| Mix-tocopherole, 70% dry matter | 16.1 g |

The suspension was converted into a powder by spray-cooling.

The product was analyzed with respect to its contents of total β-carotene, all-trans β-carotene, i.e. the amount of β-carotene on trans form, and particle size. The results thus obtained will appear from Table 1.

Examples 2–4

A suspension of

| | |
|---|---|
| Water | 1050.0 g |
| Gelatine 240 bloom, acid-hydrolyzed | 186.8 g |
| Sodium ascorbate | 25.0 g |
| β-Carotene crystals | 250.0 g | milled in a pearl mill to obtain β-carotene particles having an average particle size of below 10 μm was subjected to high-temperature heating by steam injection under pressure and subsequent cooling to 65° C. and pressure relief to atmospheric pressure under the conditions set forth in Table 1 below.

The milled and heat-treated suspensions were then mixed with a matrix solution having the following composition:

| | |
|---|---|
| Water | 300.0 g |
| Gelatine 240 bloom, acid-hydrolyzed | 181.5 g |
| Sugar | 162.5 g |
| Sodium ascorbate | 7.8 g |

The suspension was converted into a powder by spray-cooling.

The product was analyzed with respect to its contents of total β-carotene, all-trans β-carotene, particle size and crystallinity. The results obtained will appear from Table 1.

TABLE 1

| No. | High temp. conditions Time (sec) | High temp. conditions Temp. (°C.) | Total β-Carotene content (%) | All-trans β-Carotene[1] (%) | Crystal- linity (%) | Particle size d (0,5) |
|---|---|---|---|---|---|---|
| 1 | 15 | 190 | 10,5 | 63 | —[2] | 0,50 |
| 2 | 3 | 182 | 9,3 | 79 | 56 | 0,34 |
| 3 | 2,5 | 180 | 10,8 | 65 | 36 | 0,34 |
| 4 | 0,3 | 187 | 11,1 | 66 | 14 | 0,34 |
| 5 | untreated | | 9.2 | 93 | 100 | 0,35 |

[1] Portion of β-carotene on trans form
[2] Not analyzed

As will appear from Table 1, the use of a high temperature enhances the conversion of β-carotene particles from a crystalline to an amorphous state.

Examples 6–7

A suspension of

| | |
|---|---|
| Water | 1200.0 g |
| Gelatine 240 bloom, acid-hydrolyzed | 431.3 g |
| Sodium ascorbate | 37.5 g |
| Canthaxanthine crystals | 375.0 g | milled in a pearl mill to obtain canthaxanthine particles having an average particle size of below 10 μm was subjected to high-temperature heating by steam injection under pressure and following pressure relief to atmospheric pressure and cooling to 65° C. under the conditions set forth in Table 2 below.

The suspension was analyzed with respect to contents of all-trans canthaxanthine and particle size. The results thus obtained will appear from Table 2.

TABLE 2

| No. | Carotenoid | High temp. conditions Time (sec) | High temp. conditions Temp. (°C.) | All-trans Canthaxanthine[1] (%) | Crystal- linity (%) | Particle size d (0,5) |
|---|---|---|---|---|---|---|
| 7 | Canthaxantine | untreated | | 97 | 100 | 0,36 |
| 8 | Canthaxantine | 25 | 195–199 | 51 | <50 | 0,36 |

[1] Canthaxantine on trans-form

The conversion of canthaxanthine crystals from a crystalline to an amorphous state obtained by the high-temperature treatment is illustrated in FIG. 2 which shows that the irregularly shaped canthaxanthine crystals have undergone a melting and have been converted into drop shaped (amorphous) particles.

We claim:

1. Process for the preparation of a powdered water-dispersible carotenoid preparation in the form of discrete carotenoid microparticles comprising the steps of milling a carotenoid in an aqueous medium in the presence of a hydrocolloid to form a suspension, heating the suspension formed by the milling to a temperature sufficiently high to cause a total or partial melting of the carotenoid, subsequently cooling the suspension, and finely dividing and drying the suspension to form a powder.

2. Process according to claim 1, wherein the suspension is heated to a temperature slightly above the melting point of the carotenoid.

3. Process according to claim 1 wherein the suspension is maintained at the high temperature for a period of from 0.05 to 200 seconds.

4. Process according to claim 1, wherein the carotenoid is β-carotene and wherein the suspension is heated to a temperature of 150°–200° C. for a period of from 5 to 150 seconds.

5. Process according to claim 1, wherein the heat-treated suspension is quickly cooled to a temperature of between room temperature and 80° C.

6. Process according to claim 1, wherein the heating of the suspension is effected under a sufficiently high pressure to prevent evaporation of the liquid.

7. Process according to claim 1, wherein the hydrocolloid used is gelatine.

8. Process according to claim 1, including the step of adding an aqueous hydrocolloid solution to the heat-treated suspension before it is finely divided and dried.

9. Process according to claim 3, wherein the suspension is maintained at the high temperature for 0.2 to 100 seconds.

* * * * *